United States Patent
Lawrence et al.

[11] Patent Number: 5,108,992
[45] Date of Patent: Apr. 28, 1992

[54] MACROLIDE COMPOUNDS

[75] Inventors: Gordon C. Lawrence, Burnham; Michael J. Dawson, Ickenham; David Noble, Stock Mandeville; Richard A. Fletton, Ruislip; Stephen J. Lane, Eastcote, all of England

[73] Assignee: American Cyanamid Company, Stamford, Conn.

[21] Appl. No.: 630,438

[22] Filed: Dec. 20, 1990

Related U.S. Application Data

[63] Continuation of Ser. No. 360,541, Jun. 2, 1989, abandoned.

Foreign Application Priority Data

Jun. 3, 1988 [GB] United Kingdom ............... 8813150

[51] Int. Cl.[5] .................. A61K 31/365; C07D 493/22
[52] U.S. Cl. ..................... 514/30; 549/264; 514/292; 536/7.1; 548/407
[58] Field of Search ............ 549/264; 536/7.1; 514/30, 292; 548/407

[56] References Cited

U.S. PATENT DOCUMENTS

| | | | |
|---|---|---|---|
| 4,696,945 | 9/1987 | Frei et al. | 514/450 |
| 4,857,509 | 8/1989 | Frei et al. | 514/450 |
| 4,900,753 | 2/1990 | Sutherland et al. | 514/450 |
| 4,910,219 | 3/1990 | Sutherland et al. | 514/450 |
| 4,912,090 | 3/1990 | Yanai et al. | 514/450 |
| 4,916,154 | 4/1990 | Asato et al. | 514/450 |
| 4,918,096 | 4/1990 | Ramsey et al. | 514/450 |
| 4,918,098 | 4/1990 | Ramsey et al. | 514/450 |

Primary Examiner—Ronald W. Griffin
Attorney, Agent, or Firm—Bacon & Thomas

[57] ABSTRACT

Compounds of formula (1)

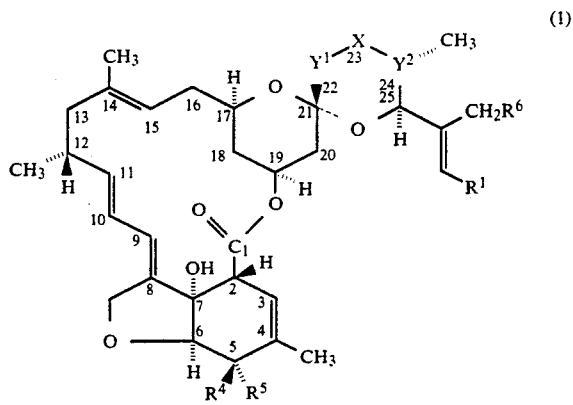

and their salts, wherein
$R^1$ is a methyl, ethyl or isopropyl group each substituted by a hydroxyl group or $R^1$ is a group $-(CH_2)_nR^7$ or a group $-CH(CH_3)R^7$ (where n is zero or 1 and $R^{7\prime}$ is $CHO$ or $CO_2H$);
$Y^1$ is $-CH_2-$, $Y^2$ is $-CH-$ and X represents

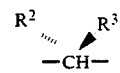

[where $R^2$ is a hydrogen atom or a group $OR^8$ is a hydroxyl group or a substituted hydroxyl group having up to 25 carbon atoms) and $R^3$ is a hydrogen atom, or $R^2$ and $R^3$ together with the carbon atom to which they are attached represent $>=O$, $>C=CH_2$ or $>C=NOR^9$ (where $R^9$ is a hydrogen atom or a $C_{1-8}$ alkyl or $C_{3-8}$ alkenyl group) and the group $>C=NOR^9$ is in the E configuration] or $-Y^1-X-Y^2-$ represents $-CH=CH-CH-$ or $-CH_2-CH=C-$;
$R^4$ is a group $OR^8$ as defined above and $R^5$ is a hydrogen atom, or $R^4$ and $R^5$ together with the carbon atom to which they are attached represent $>C=O$ or $>C=NOR^{9a}$ (where $R^{9a}$ is as defined above for $R^9$); and
$R^6$ is a hydrogen atom or a hydroxyl group. The compounds may be used to control nematode, acarine, insect or other pests.

8 Claims, No Drawings

MACROLIDE COMPOUNDS

This application is a continuation of application Ser. No. 07/360,541, filed Jun. 2, 1989, now abandoned.

This invention relates to novel macrolide compounds, to processes for their preparation and to compositions containing them.

In our UK Patent Specification 2166436 we describe the production of a class of substances, which we have designated Antibiotics S541, which may be isolated from the fermentation products of a novel Streptomyces sp. In UK Patent Specification 2176182 and European Patent Specification 215654 we describe Antibiotics S541 derivatives prepared from Antibiotics S541 by chemical and biochemical means. We have now found a further group of compounds which may be prepared from compounds described in the aforementioned UK Patent Specifications. Compounds according to the invention have antibiotic activity as described below and also are of particular use as intermediates in the preparation of other compounds having antibiotic activity.

Thus, according to one aspect of the present invention we provide the compounds of formula (1)

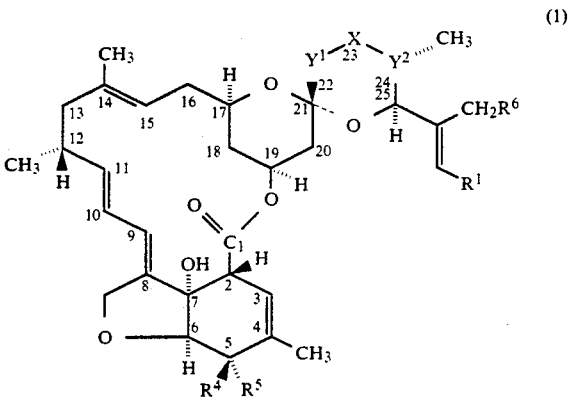

and salts thereof, wherein $R^1$ represents a methyl, ethyl or isopropyl group each substituted by a hydroxyl group or $R^1$ is a group —$(CH_2)nR^7$ or a group —$CH(CH_3)R^7$ (where n is zero or 1 and $R^7$ is a group selected from CHO and $CO_2H$);

$Y^1$ is —$CH_2$—, $Y^2$ is —CH— and X represents

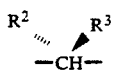

[where $R^2$ represents a hydrogen atom or a group $OR^8$ (where $OR^8$ is a hydroxyl group or a substituted hydroxyl group having up to 25 carbon atoms) and $R^3$ represents a hydrogen atom, or $R^2$ and $R^3$ together with the carbon atom to which they are attached represent >C=O, >C=CH$_2$ or >C=NOR$^9$ (where $R^9$ represents a hydrogen atom, a $C_{1-8}$ alkyl group or a $C_{3-8}$ alkenyl group) and the group >C=NOR$^9$ is in the E configuration] or —$Y^1$—X—$Y^2$— represents —CH=CH—CH— or —$CH_2$—CH=C—;

$R^4$ represents a group $OR^8$ as defined above and $R^5$ represents a hydrogen atom, or $R^4$ and $R^5$ together with the carbon atom to which they are attached represent >C=O or >C=NOR$^{9a}$ (where $R^{9a}$ is as defined above for $R^9$); and $R^6$ represents a hydrogen atom or a hydroxyl group.

The group $R^8$ when present in compounds of formula (I) may represent an acyl group e.g. a group of the formula $R^{10}CO—$ or $R^{10}OCO—$ or $R^{10}OCS—$ (where $R^{10}$ is an aliphatic, araliphatic or aromatic group, for example an alkyl, alkenyl, alkynyl, cycloalkyl, aralkyl or aryl group), a formyl group, a group $R^{11}$ which is as defined above for $R^{10}$, a group $R^{12}SO_2—$ (where $R^{12}$ is a $C_{1-4}$ alkyl or $C_{6-10}$ aryl group), a silyl group, a cyclic or acyclic acetal group, a group —$CO(CH_2)_nCO_2R^{13}$ (where $R^{13}$ is a hydrogen atom or a group as defined above for $R^{10}$ and n represents zero, 1 or 2) or a group $R^{14}R^{15}NCO—$ (where $R^{14}$ and $R^{15}$ may each independently represent a hydrogen atom or a $C_{1-4}$ alkyl group).

Where $R^{10}$ or $R^{11}$ are alkyl groups, they may be for example $C_{1-8}$ alkyl groups, e.g. methyl, ethyl, n-propyl, i-propyl, n-butyl, i-butyl, t-butyl or n-heptyl which alkyl groups may also be substituted. Where $R^{10}$ is a substituted alkyl group it may be substituted by, for example, one or more, e.g. two or three, halogen atoms (e.g. chlorine or bromine atoms), or a carboxy, $C_{1-4}$ alkoxy (e.g. methoxy, ethoxy), phenoxy or silyloxy group. Where $R^{11}$ is a substituted alkyl group it may be substituted by a cycloalkyl e.g. cyclopropyl group.

Where $R^{10}$ and $R^{11}$ are alkenyl or alkynyl groups, they preferably have 2-8 carbon atoms and where $R^{10}$ and $R^{11}$ are cycloalkyl groups, they may be for example $C_{3-12}$ cycloalkyl, such as $C_{3-7}$ cycloalkyl, e.g. cyclopentyl groups.

Where $R^{10}$ and $R^{11}$ are aralkyl groups, they preferably have 1-6 carbon atoms in the alkyl moiety, and the aryl group(s) may be carbocyclic or heterocyclic and preferably contain 4-15 carbon atoms e.g. phenyl. Examples of such groups include phen $C_{1-6}$ alkyl e.g. benzyl groups.

Where $R^{10}$ and $R^{11}$ are aryl groups, they may be carbocyclic or heterocyclic and preferably have 4-15 carbon atoms e.g. phenyl.

When $R^8$ is a group $R^{12}SO_2—$, it may be for example a methylsulphonyl or p-toluenesulphonyl group.

Where $R^8$ represents a cyclic acetal group, it may for example have 5-7 ring members as in the tetrahydropyranyl group.

When $R^8$ represents a silyl group or $R^{10}$ contains a silyloxy substituent, the silyl group may carry three groups which may be the same or different, selected from alkyl, alkenyl, alkoxy, cycloalkyl, aralkyl, aryl and aryloxy groups. Such groups may be as defined above and particularly include methyl, t-butyl and phenyl groups. Particular examples of such silyl groups are trimethylsilyl and t-butyldimethylsilyl.

When $R^8$ represents a group —$CO(CH_2)_nCO_2R^{13}$, it may for example be a group —$COCO_2R^{13}$ or —$COCH_2CH_2CO_2R^{13}$ where $R^{13}$ represents a hydrogen atom or a $C_{1-4}$ alkyl group (e.g. methyl or ethyl).

When $R^8$ represents a group $R^{14}R^{15}NCO—$, $R^{14}$ and $R^{15}$ for example may each independently be a hydrogen atom or a methyl or ethyl group.

When $R^9$ or $R^{9a}$ represents a $C_{1-8}$ alkyl group it may be for example a methyl, ethyl, n-propyl, i-propyl, n-butyl, i-butyl or t-butyl group, and is preferably a methyl group.

When $R^9$ or $R^{9a}$ represents a $C_{3-8}$ alkenyl group it may be for example an allyl group.

The group $R^1$ may be, for example, $-CH_2OH$, $-CH_2CH_2OH$, $-CH(OH)CH_3$, $-CH(CH_3)CH_2OH$, $CH_3C(OH)CH_3$, $-CO_2H$, $-CH_2CO_2H$ or $-CH(CH_3)CO_2H$.

Compounds of formula (1) containing an acidic group may form salts with suitable bases. Examples of such salts include alkali metal salts such as sodium and potassium salts.

In the compounds of formula (1) $R^1$ preferably represents $-CH(CH_3)CH_2OH$, $CH_3C(OH)CH_3$ or $-CH(CH_3)CO_2H$.

$R^4$ preferably represents an acyloxy group (e.g. an acetyloxy group) or a methoxy group or, more preferably, a hydroxyl group.

An important group of compounds of formula (1) is that in which $Y^1$ is $-CH_2-$, $Y^2$ is $-CH-$ and X represents

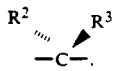

Particularly important compounds of this type are those in which $R^2$ is a hydrogen atom or a hydroxy, ethoxy or acetyloxy group and $R^3$ is a hydrogen atom or $R^2$ and $R^3$ together with the carbon atom to which they are attached represent $>C=O$, $>C=CH_2$ or $>C=NOCH_3$.

As indicated previously, compounds of the invention have antibiotic activity e.g. antihelminthic activity, for example against nematodes, and in particular, anti-endoparasitic and anti-ectoparasitic activity.

The antibiotic activity of the compounds of formula (I) may, for example, be demonstrated by their activity against parasitic nematodes such as *Caenorhabditis elegans*.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

Furthermore, the compounds of formula (I) are also of use in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae*, *Aulacorthum circumflexum*, *Myzus persicae*, *Nephotettix cincticeps*, *Nilparvata lugens*, *Panonychus ulmi*, *Phorodon humuli*, *Phyllocoptruta oleivora*, *Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla*; *Thrips tabaci*; cockroaches such as *Blatella germanica* and *Periplaneta americana* and mosquitoes such as *Aedes aegypti*.

According to the invention we therefore provide the compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or other vegetation) or to the pests themselves or a locus thereof.

The compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds of formula (I) may be formulated for use in veterinary or human medicine according to the general methods described in UK Patent Specification 2166436.

The total daily dosages of the compounds of the invention employed in both veterinary and human medicine will suitably be in the range 1–2000 $\mu g/kg$ bodyweight, preferably from 50–1000 $\mu g/kg$ and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers and diluents are as described in UK Patent Specification 2166436.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The rate at which a compound is applied depends upon a number of factors including the type of pest involved and the degree of infestation. However, in general, an application rate of 10 g/ha to 10 kg/ha will be suitable; preferably from 10 g/ha to 1 kg/ha for control of mites and insects and from 50 g/ha to 10 kg/ha for control of nematodes.

For use in veterinary medicine or for horticultural and agricultural use it may be desirable to use whole fermentation broth, as a source of the active compound. It may also be suitable to use dried broth (containing mycelia) or to use mycelia separated from the broth and pasteurised or more preferably, dried e.g. by spray-, freeze-, or roller drying. If desired the broth or mycelia may be formulated into compositions including conventional inert carriers, excipients or diluents as described above.

The antibiotic compounds of the invention may be administered or used in combination with other active ingredients.

In particular, the antibiotic compound of the invention may be used together with other antibiotic compounds. This may occur, for example, where whole fermentation broth is used without prior separation of compounds of the invention or where crude fermentation products are reacted according to the fermentation process of the invention without prior or subsequent separation; this may be preferable for example in agricultural use of a compound, where it is important to maintain low production costs.

The compounds according to the invention may be prepared by a number of processes as described in the following where $R^1$, $R^4$, $R^5$, $R^6$, $X,Y^1$ and $Y^2$ are as defined for general formula (1) unless specified otherwise. In some of these processes it may be necessary to protect one or more of any hydroxyl groups present in the starting material prior to effecting the reaction described. In such cases it may then be necessary to deprotect the same hydroxyl group(s) once the reaction has occurred to obtain the desired compound of the invention. Conventional methods of protection and deprotection may be used, for example, as described in 'Protective Groups in Organic Synthesis' by Theodora W. Greene (Wiley-Interscience, New York 1981) and 'Protective Groups in Organic Chemistry' by J. F. W. McOmie (Plenum Press, London 1973). Thus, for example, an acyl group such as an acetyl group may be removed by basic hydrolysis e.g. using sodium hydroxide or potassium hydroxide or ammonia in an aqueous alcohol such as methanol.

Thus, according to another aspect of the invention, we provide a process for preparing a compound of formula (1) which comprises incubating a compound of formula (2)

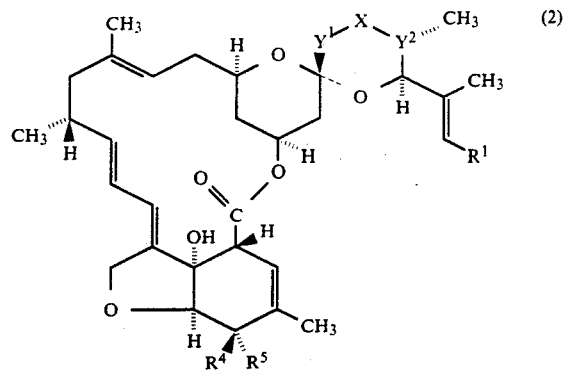

(where X, $Y^1$, $Y^2$, $R^4$ and $R^5$ are as defined above and $R^1$ is a methyl, ethyl or isopropyl group) in a suitable medium in the presence of a microorganism or an enzyme derived therefrom or a preparation derived from a microorganism containing an enzyme capable of effecting the conversion.

Suitable microorganisms and extracts thereof for use in the process according the invention may be identified by preliminary small scale tests designed to demonstrate ability of a microorganism or an extract thereof to convert compounds of formula (2) to compounds of formula (1). The formation of the compounds of formula (1) may be confirmed by suitable chromatographic analysis (e.g. high performance liquid chromatography) of the reaction mixture.

We have found microorganisms of the genus Streptomyces and extracts thereof to be particularly suitable for use in the process according to the present invention.

Particular Streptomyces microorganisms for use in the process according to the invention include strains of *Streptomyces avermitilis, Streptomyces cirratus, Streptomyces halstedii, Streptomyces antibioticus, Streptomyces lavendulae, Streptomyces alboniger, Streptomyces fimbriatus, Streptomyces felleus, Streptomyces eurythermus, Streptomyces luteogriseus, Streptomyces rimosus, Streptomyces cattley, Streptomyces albus var. ghye, Streptomyces griseus, Streptomyces plicatus, Streptomyces oganonensis, Streptomyces roseochromogenes* and *Streptomyces platensis*, and mutants of these strains.

Particularly suitable Streptomyces microorganisms for use in the process according to the invention include strains of *Streptomyces avermitilis* and *Streptomyces eurythermus* e.g. *Streptomyces avermitilis* ATCC 31272 and *Streptomyces eurythermus* ISP 5014 and mutants thereof.

Mutants of the above strains may arise spontaneously or may be produced by a variety of methods including those described in UK Patent Specification 2166436.

Other bacteria which may be used include *Nocardia orientalis, Pseudomonas putida, Pseudomonas aeruginosa, Pseudomonas fluorescens, Pseudomonas oleovarans, Mycobacterium rhodochrous, Micrococcus flavoroseus, Aerobacter aerogenes* and *Corynebacterium simplex*.

Other microorganisms which may be used in the process according to the invention include fungi and plant cell preparations.

Examples of particular fungi for use in the process according to the invention include *Penicillium oxalicum, Aspergillus clavatus, Rhizopus nigricans, Calonectria de-* cora, *Aspergillus ochraceus, Cunninghamella elegans, Gymnoascus reesii, Rhizopus arrhizus, Rhizoctonia muneratii, Calderiella acidophila, Curvularia clavata, Giberella fujikuroi, Absidia orchidis, Absidia cylindrospora, Syncephalastrum racemosum, Cunninghamella blakesleeana, Cunninghamella echinulata, Mucor hiemlis, Cladosporium herbarum, Helicostylum piriforme, Botryodiploidia theobromae, Curvalaria lunata, Clostridium absonum, Botryodiploidia malorum, Penicillium janthinellum, Pellicularia filamentosa, Aspergillus fumigatus, Hyphoderma, roseum Aspergillus phoenicis, Aspergillus niger, Aspergillus giganteus, Glomerulus cingulata, Colletotrichum lini, Cochliobolus lunatus, Tieghemella orchidis, Cereospora kaki, Fusarium ciliatum, Fusarium lini, Fusarium oxysporum, Colletotrichum phomoides, Helminthosporium sativum, Giberella zeae, Leptoporus fissilis, Penicillium lilacinum* and *Nigrospora sphaerica*. A particularly suitable fungus for use in the process according to the invention is *Absidia cylindrospora*.

Examples of plant cell preparations for use in the process according to the invention include *Phaseolus vulgaris* L., *Citrus paradisi, Nicotiana tabacum* L., *Coptis japonica, Digitalis purpurea* and *Dioscorea tokoro*.

The bioconversion may also be effected using an organism containing the genetic material of one of the aforementioned microorganisms that participates in the synthesis of the compound of formula (1). Such organisms may be obtained using genetic engineering techniques including those outlined by D. A. Hopwood in 'Cloning genes for Antibiotic Biosynthesis in Streptomyces Spp.: Production of a hybrid antibiotic' p 409–413 in Microbiology 1985, Ed. L. Lieve, American Society of Microbiology, Washington D.C. 1985. Such techniques may be used in a similar manner to that described previously for cloning antibiotic biosynthetic genes, including the biosynthetic genes for actinorhodin (Malpartida, F. and Hopwood, D. A. 1984, Nature 309, p 462–464), erythromycin (Stanzak, R. et al, 1986, Biotechnology, 4, p 229–232) and an important enzyme involved in penicillin and cephalosporin production in *Acremonium chrysogenum* (Sansom, S. M. et al, 1985, Nature, 318, p 191–194).

Suitable enzymes for use in the process according to the present invention may be derived from an extremely wide range of sources. The aforementioned Streptomyces microorganisms, however, represent a particularly suitable source of enzymes capable of converting compounds of formula (2) into compounds of formula (1).

In one embodiment of the process according to the invention, the conversion of a compound of formula (2) into a compound of formula (1) may be effected by feeding the compound of formula (2) e.g. in a suitable solvent into a fermentation medium comprising the aforementioned microorganism in the presence of assimilable sources of carbon, nitrogen and mineral salts. Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt manganese, vanadium, chromium, calcium, copper, molybdenum, boron, phosphate, sulphate, chloride and carbonate ions.

An antifoam may be present to control excessive foaming and added at intervals as required.

The compound of formula (2) in a solvent such as a water miscible organic solvent (e.g. an alcohol such as methanol or propan-2-ol, a diol such as propan-1,2-ol or butan-1,3-ol, a ketone such as acetone, a nitrile such as acetonitrile, an ether such as tetrahydrofuran or dioxan, a substituted amide such as dimethylformamide or a dialkylsulphoxide such as dimethylsulphoxide) may be added at the beginning of the cultivation, or more usually, when the growth of the microorganism is under way, e.g. 2 to 4 days after the start of the cultivation.

Cultivation of the organism will generally be effected at a temperature of from 20° to 50° C., preferably from 25° to 40° C., and will desirably take place with aeration and agitation e.g. by shaking or stirring. The medium may initially be inoculated with a small quantity of a suspension of the sporulated microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 4.0 to 9.5, preferably 5.5 to 8.5 when a Streptomyces organism is used and preferably 4.0 to 8.5 when other bacteria or a fungus are used.

Once the compound of formula (2) has been added to the culture, usually with gentle mixing, the cultivation is continued such that the desired product is accumulated. The presence of the product in the fermentation broth may be determined by monitoring extracts of the broth by high performance liquid chromatography, and uv spectroscopy at 238 nm.

The product(s) may be isolated from the whole fermentation broth by conventional isolation and separation techniques as described in UK Patent Specifications 2166436 and 2176182.

When plant cells are used as part of the fermentation process it is preferable for the cultivation to be carried out using a plant medium containing a plant cell growth regulator such as indole acetic acid, naphthalene acetic acid, indole butyric acid, 2,4-dichlorophenoxyacetic acid, kinetin or benzylamino purine at a temperature of from 15° to 35° C. with the pH maintained within the range 5.0 to 7.5. Ammonium salts and nitrates also constitute the preferred sources of nitrogen present in the fermentation medium. Sucrose, fructose and glucose also constitute the preferred sources of carbon present in the fermentation medium.

In a further embodiment of the process according to the invention, the conversion of a compound of formula (2) into a compound of formula (1) may be effected by combining and incubating a compound of formula (2) e.g. in a suitable solvent (e.g. a water miscible organic solvent as previously defined) with a preparation of an enzyme capable of effecting the conversion, desirably in a buffer solution, at, for example, 0° to 60°, preferably 20° to 40° e.g. about 28° C. The reaction will generally be carried out in the pH range 3.5 to 8.5 e.g. 5.5 to 7.5. If desired the reaction may be carried out in the presence of a cofactor such as NADH or NADPH. When the reaction is complete, i.e. when the compound of formula (2) is no longer converted to the compound of the invention (as determined by monitoring extracts of the reaction mixture by high performance liquid chromatography and uv spectroscopy at 238 nm) the product is recovered by conventional isolation and separation techniques as described in UK Patent Specifications 2166436 and 2176182.

The enzyme for use in the process of the present invention may be prepared, for example, by culture of a microorganism which produces the enzyme in a nutrient medium. Suitable nutrient media and fermentation conditions for the preparation of the enzyme include those previously described for the preparation of a compound of formula (1) from a compound of formula (2) in the presence of a microorganism. The time at which the required enzymic activity reaches a maximum will, of course, vary according to the microorganism used and, hence, the optimum cultivation time is desirably determined independently for each strain employed.

For microorganisms where the enzyme is extracellular, the liquid culture medium or the filtrate after removal of whole cells may be used as a source of enzyme. Where the enzyme is cell-bound it may be released for use by conventional methods such as sonication, grinding with glass beads, homogenisation, treatment with lytic enzymes or with detergents, after suspension of the cells in a suitable buffer.

The resulting preparation, either with or without removal of cell debris, may be used as a source of enzyme. It is preferred, however, to purify the enzyme further by conventional means. Batch or column chromatography with ion-exchange celluloses or affinity absorbents or other adsorbents e.g. hydroxylapatite may conveniently be employed. In addition, the enzyme may be concentrated or further purified by molecular sieve techniques e.g. ultrafiltration or salting out. In general, during purification procedures, it is desirable to maintain the pH within the range 3 to 11.

The enzyme may be employed in an immobilized form, e.g. by insolubilisation or entrappment thereof on or in a suitable matrix. Thus an extract of the enzyme may be bound or linked to an otherwise inert inorganic or organic polymer, entrapped on or in a fibre, or on or in a membrane or polymer such as polyacrylamide gel, adsorbed on an ion-exchange resin, crosslinked with a reagent such as glutaraldehyde, or occluded in an envelope such as a bead. Immobilized enzymes may advantageously be employed both in batch processes, after which the enzyme may be reused, and continuous flow processes wherein substrates pass through a column containing the immobilized enzyme.

In a further process, the compounds of formula (1) in which $OR^8$ is a substituted hydroxyl group may generally be prepared by reacting the corresponding 5- and/or 23-hydroxy compound with reagent serving to form a substituted hydroxyl group, followed if necessary by removal of any protecting groups present.

The reaction will in general be an acylation, sulphonylation, etherification, silylation or acetalation, and the reaction may be carried out according to the general methods described in UK Patent specification 2176182.

In yet a further process, the compounds of formula (1) in which $R^4$ and $R^5$ together with the carbon atom to which they are attached represent $>C=O$ may be prepared by oxidation of the corresponding 5-hydroxy compounds in which $R^4$ is a hydroxyl group.

The reaction may be effected with an oxidising agent serving to convert an allylic secondary hydroxyl group to an oxo group, whereby a compound of formula (1) is produced.

Suitable oxidising agents include, for example, transition metal oxides, such as manganese dioxide, and atmospheric oxygen in the presence of a suitable catalyst such as a finely divided metal e.g. platinum.

The oxidising agent will generally be used in excess over the stoichiometric quantity.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate. Combinations of such solvents either alone or with water may also be used.

The reaction may be carried out at a temperature of from −50° C. to +50° C., preferably from 0° to 30° C.

In another process according to the invention a compound of formula (1) in which X represents the group $>C=NOR^9$ and $R^4$ is a group $OR^8$ or $R^4$ and $R^5$ together with the carbon atom to which they are attached represent $>C=O$, or X represents

(where $R^2$ is a hydrogen atom or a group $OR^8$ and $R^3$ is a hydrogen atom or $R^2$ and $R^3$ together with the carbon atom to which they are attached represent $>C=NOR^9$) or $-Y^1-X-Y^2-$ represents $-CH=CH-CH-$ or $-CH_2-CH=C-$ and $R^4$ and $R^5$ together with the carbon atom to which they are attached represent $>C=NOR^{9a}$ (but excluding compounds in which $R^7$ is a group CHO) may be prepared from the corresponding 5 and/or 23-keto compounds of formula (1) by reaction with a reagent $H_2NOR^9$ (where $R^9$ is as previously defined).

The oximation reaction may conveniently be effected at a temperature in the range −20° to +100° C., e.g. −10° to +50° C. It is convenient to use the reagent $H_2NOR^9$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosphoramide), ethers (e.g. cyclic cyclic ethers such as tetrahydrofuran or dioxan, and acrylic ethers such as dimethoxyethane or diethylether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

It will be appreciated that when the compounds of formula (1) in which X represents >C=NOR$^9$ and R$^4$ and R$^5$ together with the carbon atom to which they are attached represent >C=NOR$^{9a}$ are prepared from the corresponding 5,23-diketones (i.e. compounds of formula (1) in which X represents >C=O and R$^4$ and R$^5$ together with the carbon atom to which they are attached represent >C=O) the groups >C=NOR$^9$ and >C=NOR$^{9a}$ will be the same.

In a further process according to the invention a compound of formula (1) in which X represents the group >C=O (but excluding compounds in which R$^7$ is a group CHO) may be prepared by oxidising a compound of formula (1) in which X represents

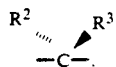

(wherein R$^2$ is a hydroxyl group and R$^3$ is a hydrogen atom), followed if necessary by removal of any protecting groups present. The reaction may be effected with an oxidising agent serving to convert a secondary hydroxyl group to an oxo group, whereby a compound of formula (1) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl choride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used.

The reaction may be carried out at a temperature of from −80° C. to +50° C.

In another process according to the invention a compound of formula (1) in which X represents >C=CH$_2$ (but excluding compounds in which R$^7$ is a group CHO or COOH) may be prepared by reacting the corresponding 23-keto compounds (i.e. compounds of formula (1) in which X represents >C=O) with an appropriate Wittig reagent e.g. a phosphorane of formula (R$^a$)$_3$P=CH$_2$ (where R$^a$ is C$_{1-6}$ alkyl or aryl e.g. monocyclic aryl such as phenyl), followed if necessary by removal of any protecting groups present. Suitable reaction solvents include ethers such as tetrahydrofuran or diethyl ether or a dipolar aprotic solvent such as dimethylsulphoxide. The reaction may be carried out at any suitable temperature e.g. at 0°.

In a further process according to the invention a compound of formula (1) in which X represents —CH$_2$— may be prepared from the corresponding 23-OH compounds [i.e. compounds of formula (1) in which X represents

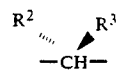

(wherein R$^2$ is a hydroxyl group and R$^3$ is a hydrogen atom)] according to the general methods described in UK Patent Specification 2176182.

In a yet further process according to the invention a compound of formula (1) in which —Y$^1$—X—Y$^2$ represents —CH=CH—CH— or —CH$_2$—CH=C— may be prepared from a corresponding 23-OH compound of formula (1) using conventional techniques, for example, as described in European Patent Specification 215654.

Salts of acids of formula (1) may be prepared by conventional methods, for example by treating the acid with a base or converting one salt into another by exchange of ion.

Intermediate compounds of formula (2) in which Y$^1$ is —CH$_2$—, Y$^2$ is —CH— and X represents

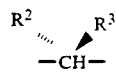

(where R$^2$ represents a hydrogen atom or a group OR$^8$ and R$^3$ represents a hydrogen atom or R$^2$ and R$^3$ together with the carbon atom to which they are attached represent >C=O) or —Y$^1$—X—Y$^2$— represents —CH=CH—CH— or —CH$_2$—CH=C— are either known compounds described in UK Patent Specifications 2166436 and 2176182 and European Patent Specification 215654 or may be prepared from such known compounds using procedures as described above.

Intermediate compounds of formula (2) in which Y$^1$ is —CH$_2$—, Y$^2$ is —CH— and X represents >C=CH$_2$ or >C=NOR$^9$ may be prepared from known compounds of formula (2) described in UK Patent Specifications 2166436 and 2176182 using the processes described above for the preparation of corresponding compounds of formula (1).

The invention is further illustrated by the following Examples wherein the compound of formula (2) above in which R$^1$ is isopropyl, Y$^1$ is —CH$_2$—, Y$^2$ is —CH—, X represents

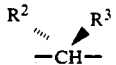

(where R$^2$ is a hydroxyl group and R$^3$ is a hydrogen atom), R$^4$ is a hydroxyl group and R$^5$ is a hydrogen atom is referred to as 'Factor A'. Compounds according to the invention are named with respect to Factor A. All temperatures are in °C.

EXAMPLE 1

Sterile water (5 ml) was added to a slope of *Streptomyces eurythermus* ISP 5014 and 1 ml portions used to inoculate 250 ml shake flasks containing the medium A (25 ml):

| | gL$^{-1}$ |
|---|---|
| D-Glucose | 2.5 |

|  | gL$^{-1}$ |
|---|---|
| Malt Dextrose MD30E | 25.0 |
| Arkasoy 50 | 12.5 |
| Molasses | 1.5 |
| KH$_2$PO$_4$ | 0.125 |
| Calcium carbonate | 1.25 |
| [3-(N-Morpholino)propanesulphonic acid] | 21.0 |
| Distilled water | as required | pH adjusted to 6.5 with H$_2$SO$_4$ before autoclaving.

The flasks were incubated at 28° for 2 days on a rotary shaker (250 rpm) and this 2 day old culture (100 ml) was used to inoculate a 7 L fermenter containing Medium A (5 L). Incubation was continued at 28° with aeration (2 L/min) and stirring (250 rpm) and, after 2 days, a solution of Factor A (2.5 g) in methanol (50 ml) was added. The fermentation was continued for a further 7 days, and the cells removed by centrifugation and extracted with methanol. The aqueous supernatant, after removal of the cells, was adjusted to pH 2.0 with concentrated hydrochloric acid and extracted with ethyl acetate. The ethyl acetate extract was evaporated to an oil, added to the methanol extract from the cells and evaporated.

The residue was extracted with methanol (50 ml) and the resulting solution fractionated (45 ml) after a fore-run of 800 ml on a column of Sephadex LH20 (130 cm×5 cm) in methanol. Fractions 18 to 26 were combined and evaporated and the residue extracted with methanol/acetonitrile/0.1M ammonium dihydrogen phosphate (10:2:2, 12 ml) and filtered. The solution was then applied to a column of Spherisorb SS ODS-2 (250 mm×20 mm) with detection at 255 nm as 1.9 ml portions. Acetonitrile/0.1M ammonium dihydrogen phosphate (1:1) was used as eluant at a constant flow rate of 25 ml/min and peaks eluting between 12.2-12.8 min and between 14.6-15.6 min from each injection were collected and those fractions with identical elution times were pooled.

Pooled material with elution time 12.2-12.8 min was diluted with an equal volume of water and pumped back on to the column, eluted with acetonitrile, evaporated and the residue lyophilised from acetone/cyclohexane to give a compound of formula (1) in which R$^1$ is —CH(CH$_3$)CH$_2$OH, Y$^1$ is —CH$_2$—, X is

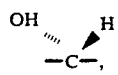

Y$^2$ is —CH—, R$^4$ is a hydroxyl group, R$^5$ is a hydrogen atom and R$^6$ is a hydrogen atom (19 mg) as a colourless solid.

A low resolution E.I. mass spectrum has a molecular ion at m/z 628 and fragment ions at 610, 592, 500, 482, 464, 425, 354, 314, 313, 281, 263, 151 and 95 mass units.

250 MHz $^1$H NMR (CDCl$_3$) includes signals at about δ0.82(d7; 3H), 1.01 (d7; 3H), 1.09(d7; 3H), 1.53(s; 3H), 1.68(s; 3H), 1.88(s; 3H), 2.71(m; 1H), 3.27(m; 1H), 3.3-3.6(m; 2H), 3.96(d6; 1H), 4.29(t6; 1H), 5.16(d9; 1H).

25.05 MHz $^{13}$C NMR (CDCl$_3$) has signals at about

| δ 173.2 (s) | 76.4 (d) |
|---|---|
| 142.6 (d) | 68.9 (d) |
| 139.2 (s) | 68.4 (?) |
| 137.6 (s) | 68.2 (?) |
| 137.3 (s) | 67.4 (?) |
| 134.8 (s) | 48.2 (t) |
| 131.6 (d) | 45.5 (d) |
| 123.2 (d) | 40.8 (t) |
| 120.1 (d) | 40.5 (t) |
| 119.9 (d) | 35.7 (?) |
| 117.8 (d) | 35.0 (d) |
| 99.6 (s) | 34.5 (t) |
| 80.0 (s) | 22.1 (q) |
| 79.1 (d) | 19.7 (q) |
|  | 16.6 (q) |
|  | 15.3 (q) |
|  | 13.9 (q) |
|  | 11.6 (q) |

By a similar method, pooled material with elution time 14.6-15.6 min gave a compound of formula (1) in which R$^1$ is

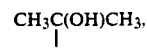

Y$^1$ is —CH$_2$—, X is

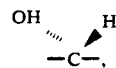

Y$^2$ is —CH—, R$^4$ is a hydroxyl group, R$^5$ is a hydrogen atom and R$^6$ is a hydrogen atom (23.5 mg) as a colourless solid.

A low resolution E.I. mass spectrum has a molecular ion at m/z 628 and fragment ions at 610, 592, 574, 482, 464, 446, 425, 381, 354, 314, 151 and 95 mass units.

250 MHz $^1$H NMR (CDCl$_3$) includes signals at about δ0.82 (d7; 3H), 1.00(d7; 3H), 1.52(s; 3H), 1.59(s; 6H), 1.84(s; 3H), 1.88(s; 3H), 3.28(m; 1H), 3.73(d11; 1H), 3.96(d6; 1H), 4.29(t6; 1H), 5.56 (s; 1H).

25.05 MHz $^{13}$C NMR (CDCl$_3$) has signals at about δ173.0 (s), 142.5 (d), 139.1(s), 137.4 (s), 137.2 (s), 136.0(d), 134.4 (s), 123.1 (d), 119.9 (d), 117.8 (d), 99.5 (s), 79.9 (s), 79.1 (d), 77.0 (d), 70.6 (s), 68.9 (d), 68.3 (?), 68.1 (?), 67.4 (d), 48.1 (t), 45.4 (d), 40.7 (t), 40.4 (t), 35.7 (?), 34.5 (t), 31.3 (q), 30.1 (q), 22.0 (q), 19.6 (q), 15.3 (q), 13.7 (q), 11.5 (q).

EXAMPLE 2

Factor A (2.5 g) in dimethylsulphoxide (50 ml) was added to a culture of *Streptomyces avermitilis* ATCC 31272 developed according to the method described in Example 1 above. The fermentation was continued for a further 5 days and the cells removed by centrifugation.

(i) The cells were stored in methanol for 16 h and then filtered to give 800 ml of filtrate. Water was added to the filtrate (to specific gravity 0.90) and the mixture was washed with hexane and evaporated to remove the methanol. The aqueous residue was extracted with ethyl acetate and the combined ethyl acetate extracts were washed with water and evaporated to give an oil. The oil was dissolved in methanol/acetonitrile/water (2:1:1, 7.5 ml), filtered, and the filtrate applied to a column of Spherisorb S5 ODS-2 (250 mm×20 mm) with detection at 238 nm as 2.5 ml portions. Acetonitrile/water (1:1) was used as eluant at a constant flow rate of 30 ml/min and peaks eluting between 10.5-12.5 min and between 25.8-26.7 min from each injection were collected and those fractions with identical elution times were combined.

Combined fractions with elution time 10.5-12.5 min were evaporated to remove acetonitrile and the aqueous residue was extracted with ethyl acetate and the ethyl acetate extract evaporated to dryness. The residue was lyophilised from acetone/cyclohexane to give a compound of formula (1) in which $R^1$ is —CH(CH$_3$)CH$_2$OH, $Y^1$ is —CH$_2$—, X is

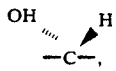

$Y^2$ is —CH—, $R^4$ is a hydroxyl group, $R^5$ is a hydrogen atom and $R^6$ is a hydrogen atom (29.6 mg) as a colourless solid which by h.p.l.c. analysis was shown to be identical to the compound obtained in Example 2 (ii) below which eluted between 15.6 and 17 min.

Combined fractions with elution time 25.8-26.7 min were diluted with an equal volume of water and pumped back on to a column of Spherisorb S5 ODS-2 (100 mm × 4.6 mm) eluting with acetonitrile. The eluate was evaporated and the residue lyophilised from acetone/cyclohexane to give a compound of formula (1) in which $R^1$ is —CH(CH$_3$)CH$_2$OH, $Y^1$ is —CH$_2$—, X is

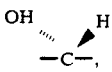

$Y^2$ is —CH—, $R^4$ is a methoxy group, $R^5$ is a hydrogen atom and $R^6$ is a hydrogen atom (4.4 mg) as a solid.

A low resolution E.I. mass spectrum has a molecular ion at m/z 642 and fragment ions at 624, 606, 482, 464, 439, 354, 314, 281, 313, 263, 151 and 95 mass units.

250 MHz $^1$H NMR (CDCl$_3$) gave signals at about $\delta$0.81(d7; 3H), 1.01 (d7; 3H), 1.07(d7; 3H), 1.52(s; 3H), 1.66(s; 3H), 1.80(s; 3H), 2.71(m; 1H), 3.31(m; 1H), 3.50(s; 3H), 3.96(d6; 1H), 4.02(d6; 1H), 4.95(m; 1H), 5.39(m; 1H).

(ii) The aqueous supernatant, after removal of the cells, was extracted with ethyl acetate and the extract evaporated to give an oil. The oil was dissolved in acetonitrile/0.1M ammonium dihydrogen phosphate (2:1, 15 ml), filtered and the filtrate applied to a column of Spherisorb S5 ODS-2 (250 mm × 20 mm) with detection at 238 nm as 4.5 ml portions. Acetonitrile/0.1M ammonium dihydrogen phosphate/water (5:5:1) was used as eluant at a constant flow rate of 30 ml/min and peaks eluting between 11.2-12.6 min and between 15.6-17 min from each injection were collected and those fractions with identical elution times were pooled.

Pooled material with elution time 11.2-12.6 min were evaporated to remove acetonitrile and the aqueous residue was extracted with ethyl acetate. The combined ethyl acetate extracts were washed with water, dried, evaporated and the residue lyophilised to give a compound of formula (1) in which $R^1$ is —CH(CH$_3$)CO$_2$H, $Y^1$ is —CH$_2$—, X is

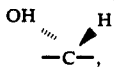

$Y^2$ is —CH—, $R^4$ is a hydroxyl group, $R^5$ is a hydrogen atom and $R^6$ is a hydrogen atom (13 mg) as a colourless solid.

A low resolution E.I. mass spectrum has a molecular ion at m/z 642 and fragment ions at 624, 606, 514, 496, 478, 442, 425, 354, 327, 314, 295, 277, 151 and 95 mass units.

I.r. (CHBr$_3$ solution) showed bands at about 3500 (OH), 1720 (CO$_2$H) and 1696 (CO$_2$R) cm$^{-1}$.

250 MHz $^1$H NMR (CDCl$_3$) includes signals at about $\delta$0.79(d7; 3H), 1.00(d7; 3H), 1.36(d7; 3H), 1.53(s; 3H), 1.68(s; 3H), 1.86(s; 3H), 3.27(m; 1H), 3.46(m; 1H), 3.94(d6; 1H), 4.29(d6; 1H), 4.96(m; 1H).

Similarly, pooled material with elution time 15.6-17 min gave a compound of formula (1) in which $R^1$ is —CH(CH$_3$)CH$_2$OH, $Y^1$ is —CH$_2$—, X is

$Y^2$ is —CH—, $R^4$ is a hydroxyl group, $R^5$ is a hydrogen atom and $R^6$ is a hydrogen atom (23 mg) as a colourless solid.

A low resolution E.I. mass spectrum has a molecular ion at m/z 628 and fragment ions at 610, 592, 500, 482, 464, 425, 354, 314, 313, 281, 263, 151 and 95 mass units.

250 MHz $^1$H NMR spectrum includes signals at about $\delta$0.81(d7; 3H), 1.00(d7; 3H), 1.08(d7; 3H), 1.53(s; 3H), 1.69(s; 3H), 1.88(s; 3H), 2.71(m; 1H), 3.27(m; 1H), 3.3-3.6(m; 2H), 3.96(d6; 1H), 4.29(d6; 1H), 5.16 (d9; 1H).

EXAMPLE 3

Factor A (2.5 g) in methanol (50 ml) was added to a culture of *Absidia cylindrospora* NNRL 2796 developed according to the method of Example 1 except that the following medium was used:

|  | $gL^{-1}$ |
| --- | --- |
| Corn steep liquor | 20.0 |
| Meritose | 10.0 |
| Soya oil | 1.0 |
| Distilled water | as required | pH adjusted to 4.8-5.0 with potassium hydroxide before autoclaving.

The fermentation was continued under the same conditions for a further 5 days and the cells removed by centrifugation. The cells were then extracted with methanol (400 ml).

The supernatant from the culture fluid was evaporated down to about 900 ml and extracted with ethyl acetate. The combined ethyl acetate extracts were evaporated and the residue dissolved in methanol (ca. 100 ml). The resulting suspension was filtered and the filtrate evaporated to dryness.

The methanolic cell extract was evaporated to an oil which was dissolved in water and extracted with ethyl acetate. The combined ethyl acetate extract was then added to the supernatant residue and the mixture dried.

The residue was dissolved in chloroform/ethyl acetate (3:1, ca. 30 ml) and loaded onto a column of Kieselgel 60 (Merck 5734, 100 ml) and fractionated (20 ml) in the same solvent. Fractions 11-32 were combined and evaporated to dryness. The column was then eluted with ethyl acetate and this solution evaporated to give a solid. The residue from fractions 11-32 was purified in four portions by preparative high performance liquid chromatography on a column of Spherisorb S5 ODS-2 eluting with acetonitrile/water (1:1) at a rate of 30 ml/min with detection at 238 nm. Peaks eluting between 19.8 and 21.3 min from each injection were collected and pooled.

Pooled material with elution time 19.8–21.3 min was diluted with an equal volume of water, pumped back onto the column and eluted with acetonitrile. The eluate was evaporated to give a solid which was lyophilised from acetone/cyclohexane to give a compound of formula (1) in which $R^1$ is —CH(CH$_3$)CH$_2$OH, $Y^1$ is —CH$_2$—, X is

$Y^2$ is —CH—, $R^4$ is a hydroxyl group, $R^5$ is a hydrogen atom and $R^6$ is a hydrogen atom (96.8 mg).

A low resolution E.I. mass spectrum has a molecular ion at m/z 628 and fragment ions at 610, 592, 500, 482, 464, 425, 354, 314, 313, 281, 263, 151 and 95 mass units.

250 MHz $^1$H NMR (CDCl$_3$) includes signals at about δ0.82(d7; 3H), 0.98(d7; 3H), 1.01(d7; 3H), 1.54(s; 3H), 1.58(s; 3H), 1.68(s; 3H), 1.88(s; 3H), 2.71(m; 1H), 3.26(m; 1H), 3.96(d6; 1H), 4.29(t6; 1H), 4.97(m; 1H), 5.20(d9; 1H).

Similar treatment of the ethyl acetate eluate from silica but with a developing solvent of acetonitrile:water (4:6) at 25 ml/min gave a peak eluting between 20.0–22.6 min which, after recovery, gave a compound of formula (1) in which $R^1$ is —CH(CH$_3$)CH$_2$OH, $Y^1$ is —CH$_2$—, X is

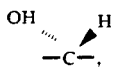

$Y^2$ is —CH—, $R^4$ is a hydroxyl group, $R^5$ is a hydrogen atom and $R^6$ is a hydroxyl group (33.6 mg)

A low resolution E.I. mass spectrum has a molecular ion at m/z 644 and fragment ions at 626, 608, 590, 516, 498, 480, 462, 425, 354, 314, 151 and 95 mass units.

250 MHz $^1$H NMR (CDCl$_3$) includes signals at about δ0.84(d7; 3H), 1.01(d6; 6H), 1.53(s; 3H), 1.87(s; 3H), 3.24(m; 1H), 3.94(d6; 1H), 4.03(d10; 1H), 4.14(d11; 1H), 4.24(d11; 1H), 5.01(m; 1H), 5.18(m; 1H).

62.5 MHz $^{13}$C NMR (CDCl$_3$) gave signals at about

| δ 172.8 (s) | 68.1 (?) |
|---|---|
| 142.6 (d) | 67.5 (?) |
| 139.2 (s) | 67.0 (?) |
| 137.6 (s) | 66.7 (t) |
| 137.4 (d) | 57.2 (t) |
| 137.1 (s) | 48.3 (t) |
| 123.3 (d) | 45.6 (d) |
| 120.3 (d) | 40.8 (t) |
| 119.9 (d) | 40.7 (t) |
| 117.9 (d) | 36.5 (d) |
| 99.8 (s) | 35.8 (?) |
| 80.1 (s) | 35.7 (?) |
| 79.3 (d) | 35.2 (d) |
| 76.5 (d) | 34.5 (t) |
| 73.2 (t) | 22.1 (q) |
| 72.8 (t) | 19.6 (q) |
| 69.0 (d) | 17.2 (q) |
| 68.6 (d) | 15.3 (q) |
|  | 14.0 (q) |

The following are examples of formulations according to the invention. The term 'Active Ingredient' as used hereinafter means a compound of the invention.

MULTIDOSE PARENTERAL INJECTION

EXAMPLE 1

|  | % w/v | Range |
|---|---|---|
| Active ingredient | 2.0 | 0.1–6.0% w/v |
| Benzyl alcohol | 1.0 |  |
| Polysorbate 80 | 10.0 |  |
| Glycerol formal | 50.0 |  |
| Water for Injections | to 100.0 |  |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

EXAMPLE 2

|  | % w/v | Range |
|---|---|---|
| Active ingredient | 4.0 | 0.1–7.5% w/v |
| Benzyl alcohol | 2.0 |  |
| Glyceryl triacetate | 30.0 |  |
| Propylene glycol | to 100.0 |  |

Dissolve the active ingredient in the benzyl alcohol and glyceryl triacetate. Add the propylene glycol and make up to volume. Sterilize the product by conventional pharmaceutical methods, for example sterile filtration, and package aseptically.

EXAMPLE 3

|  | % | Range |
|---|---|---|
| Active ingredient | 2.0 w/v | 0.1–7.5% w/v |
| Ethanol | 36.0 v/v |  |
| Non-ionic surfactant | 10.0 w/v |  |
| (e.g. Synperonic PE L44*) |  |  |
| Propylene glycol | to 100.0 |  |

*Trademark of ICI

Dissolve the active ingredient in the ethanol and surfactant and make up to volume. Sterilize the product by conventional pharmaceutical methods, for example sterile filtration, and package aseptically.

EXAMPLE 4

|  | % | Range |
|---|---|---|
| Active Ingredient | 2.0 w/v | 0.1–3.0% w/v |
| Non-ionic surfactant | 2.0 w/v |  |
| (e.g. Synperonic PE F68*) |  |  |
| Benzyl alcohol | 1.0 w/v |  |
| Miglyol 840** | 16.0 v/v |  |
| Water for Injections | to 100.0 |  |

*Trademark for ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

Aerosol Spray

|  | % w/w | Range |
|---|---|---|
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

TABLET

Method of Manufacture—Wet Granulation

|  | mg |
|---|---|
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose | to tablet core weight of 450 mg |

Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

VETERINARY TABLET FOR SMALL/DOMESTIC ANIMAL USE

Method of Manufacture—Dry Granulation

|  | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

VETERINARY INTRAMMARY INJECTION

|  |  | mg/dose | Range |
|---|---|---|---|
| Active Ingredient | | 150 mg | 0.05–1.0 g |
| Polysorbate 60 | 3.0% w/w | | |
| White Beeswax | 6.0% w/w | to 3 g | to 3 or 15 g |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

VETERINARY SLOW-RELEASE BOLUS

|  | % w/w | Range |
|---|---|---|
| Active Ingredient | | 0.25–2 g |
| Colloidal silicon dioxide | 2.0 | to required |
| Microcrystalline cellulose | to 100.0 | fill weight |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient.

VETERINARY ORAL DRENCH

|  | % w/v | Range |
|---|---|---|
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

VETERINARY ORAL PASTE

|  | % w/w | Range |
|---|---|---|
| Active Ingredient | 4.0 | 1–20% w/w |
| Saccharin sodium | 2.5 | |
| Polysorbate 85 | 3.0 | |
| Aluminium distearate | 5.0 | |
| Fractionated coconut oil | to 100.0 | |

Disperse the aluminium distearate in the fractionated coconut oil and polysorbate 85 by heating. Cool to room temperature and disperse the saccharin sodium in the oily vehicle. Disperse the active ingredient in the base. Fill into plastic syringes.

GRANULES FOR VETERINARY IN-FEED ADMINISTRATION

|  | % w/w | Range |
|---|---|---|
| Active Ingredient | 2.5 | 0.05–5% w/w |
| Calcium sulphate. hemi-hydrate | to 100.0 | |

Blend the Active Ingredient with the calcium sulphate. Prepare the granules using a wet granulation process. Dry using a tray or fluid-bed drier. Fill into the appropriate container.

VETERINARY POUR-ON

|  | % w/v | Range |
|---|---|---|
| Active Ingredient | 2.0 | 0.1 to 30% |
| Dimethyl sulphoxide | 10.0 |  |
| Methyl Isobutyl ketone | 30.0 |  |
| Propylene glycol (and pigment) | to 100.0 |  |

Dissolve the active ingredient in the dimethyl sulphoxide and the methyl isobutyl ketone. Add the pigment and make up to volume with the propylene glycol. Fill into the pour-on container.

EMULSIFIABLE CONCENTRATE

| Active ingredient | 50 g |
|---|---|
| Anionic emulsifier (e.g. Phenyl sulphonate CALX) | 40 g |
| Non-ionic emulsifier (e.g. Synperonic NP13) * | 60 g |
| Aromatic solvent (e.g. Solvesso 100) to | 1 liter. |

* Trademark of ICI

Mix all ingredients, stir until dissolved.

GRANULES

| (a) | Active ingredient | 50 g |
|---|---|---|
|  | Wood resin | 40 g |
|  | Gypsum granules (20-60 mesh) to (e.g. Agsorb 100A) | 1 kg |
| (b) | Active ingredient | 50 g |
|  | Synperonic NP13 * | 40 g |
|  | Gypsum granules (20-60 mesh) to | 1 kg. |

* Trademark for ICI

Dissolve all ingredients in a volatile solvent e.g. methylene chloride, add to granules tumbling in mixer. Dry to remove solvent.

We claim:

1. Compounds of formula (1)

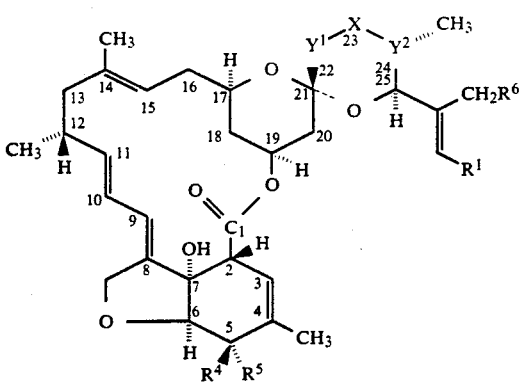

and their salts, wherein

R$^1$ is a methyl, ethyl or isopropyl group each substituted by a hydroxyl group or R$^1$ is a group —(CH$_2$)$_n$R$^7$ or a group —CH(CH$_3$)R$^7$ (wherein n is zero or 1 and R$^7$ is CHO or CO$_2$H); Y$^1$ is —CH$_2$—, Y$^2$ is —CH— and X represents

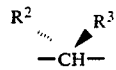

wherein R$^2$ is a hydrogen atom or a group OR$^8$ wherein OR$^8$ is a hydroxyl group or a substituted hydroxyl group having up to 25 carbon atoms and R$^3$ is a hydrogen atom, or R$^2$ and R$^3$ together with the carbon atom to which they are attached represent >C=O, >C=CH$_2$ or >C=NOR$^9$ (wherein R$^9$ is a hydrogen atom or a C$_{1-8}$ alkyl or C$_{3-8}$ alkenyl group) and the group >C=NOR$^9$ is in the E configuration or —Y$^1$—X—Y$^2$— represents —CH=CH—CH— or —CH$_2$—CH=C—;

R$^4$ is a group OR$^8$ as defined above and R$^5$ is a hydrogen atom, or R$^4$ and R$^5$ together with the carbon atom to which they are attached represent >C=O or >C=NOR$^{9a}$ (wherein R$^{9a}$ is as defined above for R$^9$); and R$^6$ is a hydrogen atom or a hydroxyl group.

2. Compounds according to claim 1 in which R$^1$ is —CH(CH$_3$)CH$_2$OH, —C(OH)(CH$_3$)$_2$ or —CH(CH$_3$)COOH.

3. Compounds according to claim 1 in which Y$^1$ is —CH$_2$—, Y$^2$ is —CH— and X represents —C(R$^2$)(R$^3$)— wherein R$^2$ is a hydrogen atom or a hydroxy, ethoxy or acetyloxy group and R$^3$ is a hydrogen atom or R$^2$ and R$^3$ together with the carbon atom to which they are attached represent >C=O, >C=CH$_2$ or >C=NOCH$_3$; and R$^4$ is a hydroxy, methoxy or acetyloxy group.

4. Compounds according to claim 1, in which;

R$^1$ is —CH(CH$_3$)CH$_2$OH, Y$^1$ is —CH$_2$—, X is —CR$^2$R$^3$— wherein R$^2$ is —OH and R$^3$ is a hydrogen atom, Y$^2$ is —CH—, R$^4$ is a hydroxyl group, R$^5$ is a hydrogen atom and R$^6$ is a hydrogen atom;

R$^1$ is —C(OH)(CH$_3$)$_2$, Y$^1$ is —CH$_2$—, X is —CR$^2$R$^3$— wherein R$^2$ is —OH and R$^3$ is a hydrogen atom, Y$^2$ is —CH—, R$^4$ is a hydroxyl group, R$^5$ is a hydrogen atom and R$^6$ is a hydrogen atom;

R$^1$ is —CH(CH$_3$)CH$_2$OH, Y$^1$ is —CH$_2$—, X is —CR$^2$R$^3$— wherein R$^2$ is —OH and R$^3$ is a hydrogen atom, Y$^2$ is —CH—, R$^4$ is a methoxy group, R$^5$ is a hydrogen atom and R$^6$ is a hydrogen atom;

R$^1$ is —CH(CH$_3$)CO$_2$H, Y$^1$ is —CH$_2$—, X is —CR$^2$R$^3$— wherein R$^2$ is —OH and R$^3$ is a hydrogen atom, Y$^2$ is —CH—, R$^4$ is a hydroxyl group, R$^5$ is a hydrogen atom and R$^6$ is a hydrogen atom; or R$^1$ is —CH(CH$_3$)CO$_2$H, Y$^1$ is —CH$_2$—, X is —CR$^2$R$^3$— wherein R$^2$ is —OH and R$^3$ is a hydrogen atom, Y$^2$ is —CH—, R$^4$ is a hydroxyl group, R$^5$ is a hydrogen atom and R$^6$ is a hydroxyl group.

5. A pharmaceutical composition containing a pesticidally effective amount of at least one compound according to claim 1 together with a pharmaceutically acceptable carrier.

6. A veterinary composition containing a pesticidally effective amount of at least one compound according to claim 1 and a veterinary acceptable carrier.

7. A pesticidal composition containing a pesticiendally effective amount of a compound according to claim 1 and a pesticidally acceptable carrier.

8. A method of combatting insect, acarine or nematode pests which comprises applying an amount of a compound according to claim 1 effective in combatting pests to the pests or to a locus of the pests.

* * * * *